(12) United States Patent
McEwen et al.

(10) Patent No.: US 6,168,569 B1
(45) Date of Patent: **\*Jan. 2, 2001**

(54) APPARATUS AND METHOD FOR RELATING PAIN AND ACTIVITY OF A PATIENT

(76) Inventors: James Allen McEwen, 10551 Bamberton Drive, Richmond, B.C. (CA), V7A 1K6; Alexei John Marko, 2850 Mackenzie St., Vancouver, B.C. (CA), V6K4A2; Michael Jameson, 2365 Badger Road, North Vancouver, B.C. (CA), V7G 1S9

( * ) Notice: Under 35 U.S.C. 154(b), the term of this patent shall be extended for 0 days.

(21) Appl. No.: 09/219,234

(22) Filed: Dec. 22, 1998

(51) Int. Cl.$^7$ .................................................. A61B 19/00

(52) U.S. Cl. ............................................ 600/557; 600/587
(58) Field of Search .................................. 600/557, 587, 600/595

(56) References Cited

U.S. PATENT DOCUMENTS

| | | |
|---|---|---|
| 3,797,010 | 3/1974 | Alder . |
| 4,353,375 | 10/1982 | Colburn . |
| 4,444,205 | 4/1984 | Jackson . |
| 4,576,180 | 3/1986 | Taheri . |
| 4,578,769 | 3/1986 | Frederick . |
| 4,757,453 | 7/1988 | Nasiff . |
| 4,774,679 | 9/1988 | Carlin . |
| 4,975,842 | 12/1990 | Darrow . |
| 5,086,785 | 2/1992 | Gentile et al. . |
| 5,426,595 | 6/1995 | Picard et al. . |
| 5,485,402 | 1/1996 | Smith et al. . |
| 5,524,645 | 6/1996 | Wills . |
| 5,653,739 | 8/1997 | Maurer et al. . |
| 5,692,500 | 12/1997 | Gaston-Johanson . |
| 5,724,983 | 3/1998 | Selker et al. . |
| 5,749,372 | 5/1998 | Allen et al. . |
| 5,751,214 | 5/1998 | Cowley et al. . |
| 5,755,675 | * 5/1998 | Sihvonen ............................. 600/594 |
| 5,762,072 | 6/1998 | Conlan et al. . |

FOREIGN PATENT DOCUMENTS

| | | |
|---|---|---|
| 3703404A1 | 8/1988 | (DE) . |
| 2 071 507 | 10/1979 | (GB) . |

OTHER PUBLICATIONS

International Search Report; Counterpart Application PCT/CA99/01226; Mar. 30, 2000.
William H. Harris. Traumatic Arthritis of the Hip After Dislocation and Acetabular Fractures: Treatment by Mold Arthroplasty, *The Journal of Bone and Joint Surgery*, 1969, pp. 737–755.
Steven J. Linton. The Relationship Between Activity and Chronic Back Pain, *Pain*, 1985 (vol. 21), pp. 289–294.
Nicholas Bellamy, Et Al. Validation Study of WOMAC: A Health.
Status Instrument for Measuring Clinically Important Patient Relevant Outcomes to Antirheumatic Drug Therapy in Patients with Osteoarthritis of the Hip or Knee, *The Journal of Rheumatology*, 1988, pp. 1833–1840.

A. Erskine, Et Al. Memory for Pain: A Review, *Pain*, 1990 (vol. 40), pp. 255–265.
Mary Wagner. Outcomes Research Affecting Devices, *Modern Healthcare*, p. 54.
W.B. Smith, Et Al. Effects of Present Pain Level on Recall of Chronic Pain and Medication Use, *Pain*, 1993 (vol. 55), pp. 355–361.
J.E. Ware. SF–36 Health Survey Manual Interpretation Guide, The Health Institute, New England Medical Centre, Boston, MA 1993.
B. Lewis, Et Al. Frequent Measurement of Chronic Pain: An Electronic Diary and Empirical Findings, *Pain*, 1995 (vol. 60), pp. 341–347.
Michael E. Geisser, Et Al. A Time Series Analysis of the Relationship Between Ambulatory EMG, Pain, and Stress in Chronic Low Back Pain, *Biofeedback and Self–Regulation*, vol.20, No.4, 1995, pp.339–353.
G. Affleck, Et Al. Sequential Daily Relations of Sleep, Pain Intensity, and Attention to Pain Among Women with Fibromyalgia, *Pain*, 1996 (vol.68), pp. 363–368.
Alexander A. Vendrig, Et Al. Within–Person Relationships Among Pain Intensity, Mood and Physical Activity in Chronic Pain: A Naturalistic Approach, *Pain*, 1997 (vol. 73), pp. 71–76.
Thomas P. Schmalzried, Et Al. Quantitative Assessment of Walking Activity After Total Hip or Knee Replacement, *The Journal of Bone and Joint Surgery*, 1998, pp. 54–59.
A. Marko, Et Al. Need for Improved Assessment of Patient Outcomes in Knee Arthroplasty Surgery: How Can We Get Better Value for Money? *The Canadian Medical and Biological Engineering Society: Conference Proceedings*, Jun. 1998, pp. 44–45.
C. Morin, Et Al. Temporal and Qualitative Properties of Cold Pain and Heat Pain: A Psychophysical Study, *Pain*, 1998 (vol. 74), pp. 67–73.

* cited by examiner

Primary Examiner—Cary O'Connor
Assistant Examiner—Pamela Wingood
(74) Attorney, Agent, or Firm—Ipsolon, LLP

(57) ABSTRACT

Apparatus for relating pain and activity experienced by a patient comprises: pain transducing means for allowing a patient to select any one pain level from a predetermined number of pain levels and for producing a pain level signal indicative of the selected level; activity transducing means responsive to the pain level signal for measuring a level of a parameter of a physical activity of the patient near the time corresponding to the selection of the pain level and for producing an activity parameter level signal indicative of the measured level of the parameter; and relating means responsive to the pain level signal and the activity parameter level signal for characterizing the activity of the patient corresponding to the selected level of pain to be one activity level of a predetermined number of predefined activity levels and for producing a signal indicative of the characterized level of activity and the corresponding pain level.

16 Claims, 7 Drawing Sheets

APPARATUS AND METHOD FOR RELATING PAIN AND ACTIVITY OF A PATIENT

FIELD OF INVENTION

The invention relates to apparatus and a method generally useful in quantitatively relating levels of pain and activity experienced by a human subject. The invention relates more particularly, but not by way of limitation, to apparatus and a method for characterizing the level of activity of a medical or surgical patient based on measured parameters of activity and for relating the characterized activity to corresponding levels of pain reported by the patient, wherein pain and activity are related over a period of time sufficient to be useful in more quantitatively assessing the outcome of the patient in response to any therapeutic interventions such as surgery, physical therapy, the use of therapeutic devices such as braces or the administration of drugs.

BACKGROUND OF INVENTION

Many people who suffer from debilitating conditions undergo treatment to reduce pain and to restore physical function. In order to compare the effectiveness of the various treatments for a specific condition it is desirable to quantify patient outcomes. For example, patients suffering from arthritis may undergo a variety of treatments including physiotherapy, naturopathic treatment, drug treatment, intra-articular injection and surgery in order to restore function and reduce pain in affected joints. There is a need for apparatus and methodology useful in assessing the outcomes of patients in response to such treatments, thereby allowing better "value for money" decisions to be made in the allocation of health care resources. More specifically, there is a need for apparatus and methodology useful in characterizing the activity of patients and for relating the characterized activity to corresponding levels of pain over extended periods of time, so that any changes in the nature and levels of activity and related pain of patients in response to treatments can be more quantitatively evaluated. In this way, quantification of patient outcomes from various medical treatments may be useful in helping to identify the optimal treatment, or "best practice", may also be useful in helping to identify patients who would not benefit from certain treatments, and may further be useful in evaluating staff performing such treatments.

In the field of orthopedics, patient outcomes can be measured in terms of the relief of pain and the restoration of function in a limb or joint. To assist in the assessment of the outcomes for patients in response to orthopedic treatments, there is a need for apparatus and methods to objectively measure and characterize the amount and type of activity undertaken by a patient and the relationship between this activity and associated levels of pain experienced by the patient so that any changes in response to treatments can be more objectively evaluated. Furthermore, it is desirable to determine this relationship over periods of time in which the full spectrum of activities representative of normal living by the patient may occur. There is also a need to include in such apparatus and methods means for indicating any short-term changes in the pain-activity relationship that may be related to events such as taking medications, as well as longer-term changes that may be the outcomes of various major treatments being assessed. No known apparatus or methods are known in the prior art which would meet these needs.

In the prior art, quantification of outcomes for orthopedic treatments has typically involved the use of questionnaires completed by the patient or the use of clinical instruments such as goniometers or arthrometers to measure physical parameters related to the structure of the joint. In this prior art there is no means to quantitatively measure the activity levels of an orthopedic patient over a period of time sufficient to include most of the activities of normal daily living of the patient and to relate the activity levels to corresponding levels of pain experienced by the patient.

Patient questionnaires such as the SF-36, the Western Ontario-McMaster University Osteoarthritis Index (WOMAC) and the Harris Hip Score (HHS) provide a means to generate scores indicative of disability that depend on a range of parameters including pain and activity as reported by the patient. However, no direct measurement of these parameters is undertaken and no provision is made to quantify the relationship between measured activity and the corresponding levels of pain intensity experienced by the patient. These questionnaires are typically provided as paper forms for the patient to complete. They are subject to a wide range of biases due to their subjective nature and require patients to summarize experiences over long periods of time, containing for example, questions such as "how much bodily pain have you had during the last 4 weeks" and "The following are activities you might do during a typical day—does your health now limit you in these activities?"

In the prior art there are many devices to measure and produce an indication of one component of patient activity. These include devices such as simple pedometers that provide a measure of the total number of steps taken by a subject as well as more sophisticated instruments that count steps or measure activity in terms of movement of an accelerometer type sensor applied to the patent. Typical of this prior art is that disclosed in U.S. Pat. No. 5,485,402, to Smith et al. Therein a gait activity monitor is disclosed comprising a sensor worn on the ankle, for measuring movement of the ankle relative to the environment. The monitor stores the signals from the sensor in a memory means and a processing means responsive to the movement signal provides a plurality of motion count units indicative of the number of movements that occur during consecutive measurement intervals. The device is intended to be worn over prolonged periods and includes apparatus to permit transmitting recorded data to a remote system computer for data processing. Typical of these devices, the Smith et al. patent fails to show or suggest apparatus capable of determining and recording information relating to the corresponding pain intensity experienced by the wearer during the measurement period, nor does it disclose apparatus relating to a processing means for determining the relationship between measured pain and activity and producing an indication of this relationship. Furthermore, devices found in the prior art generally only quantify one aspect of activity. Such devices do not provide a means to accurately characterize and differentiate between different types of activities normally undertaken by a patient such as reclining, standing and walking in a manner consistent with the methodology of common clinical questionnaires and as done by clinicians during patient exams and interviews.

Goniometers are also commonly used in the evaluation of orthopedic patients in order to measure and quantify the range of motion of a joint. Goniometers range from simple apparatus for measuring the angle between the two sides of a joint, to complex systems which quantify a wide range of parameters relating to range of motion of the joint and joint laxity. These devices are intended to take "snapshot" measurements and are not suitable for the dynamic measurement of joint function and activity during the activities of daily living. They are therefore of no value in assessing patient outcomes in terms of change in joint activity and associated pain.

Any report or rating of pain over a time period necessarily depends on the patient's memory of the pain experienced during the time period. Pain memory is well established as complex and problematic. Study of pain and its relation to activity involves estimates of pain over successive time periods, which are often quite lengthy and so is especially vulnerable to problems arising from reliance on memory for pain and activity data. Attempting to avoid such memory problems suggests that continuous tracking of current pain could be regarded as ideal. The most common method for measuring pain is a manually completed pain rating scale that is presented in paper form. Such a scale provides a tool to measure the magnitude or intensity of pain at an arbitrary point in time. Application of these scales is separate from the measurement of the activity being undertaken by the patient. The use of multiple pain scale measurements or written "pain diaries" has been previously established as a tool to acquire more detailed data related to pain experienced by a subject over extended periods ranging from days to years. However, such methodologies suffer from inadequacies related to their lack of convenience, problems due to cramming (i.e. patients entering data all at once in preparation for a visit to the clinic) and inherent bias caused by the observer being able to review previously entered data. Lewis et al. (1990) described the use of an electronic data logger or "electronic diary" to record pain ratings over a period of months. Lewis also suggests the possibility of incorporating a movement detector in the device in order to assess compliance with an exercise regimen, but does not suggest, nor could have predicted apparatus to acquire pain information based on measured activity, to characterize observed activity, and to produce an indication of the relationship between pain intensity experienced by the patient and the characterized activity. Vendrig et al. (1997) conducted research to investigate the relationship between pain, activity and mood in chronic pain patients, describing the use of questionnaires applied at frequent intervals in order to record mood, pain and activity levels reported subjectively by the patients. Similar work was conducted by Geisser et al. (1995) who used portable EMG recorders and visual analog scales contained in a portable notebook to record muscle activity, pain and stress in ambulatory patients for comparison. However, Vendrig et al. and Geisser et al. only describe the simple acquisition of this data using written questionnaires to be completed at the discretion of the patient at routine intervals and the subsequent manual comparison of this data but do not describe, nor could have predicted apparatus and methodology to acquire pain information based on measured activity, to characterize observed activity, and to produce an indication of the relationship between pain intensity experienced by the patient and the characterized activity. Furthermore, the methodology described by Vendrig et al. and Geisser et al. is subject to the same biases associated with lack of convenience, cramming and viewing previous data as described previously. Smith et al. (1993) suggested use of portable electronic data loggers to record ratings of chronic pain using a slider on a 10 centimeter visual analog scale, and others including Affleck et al. (1996) and Morin et al. (1998) have utilized similar apparatus to log pain scores as a function of time in patients. U.S. Pat. No. 5,692,500 to Gaston-Johansson discloses a tool for providing an indication of the pain experienced by a person using multiple sets of selection indicators and sliding scales, each being indicative of a dimension of pain. Also in the prior art is that disclosed in U.S. Pat. No. 5,653,739 to Maurer et al. Therein an electronic pain feedback system is disclosed which provides a means for recording a patient's level of pain and controlling the administration of a pain treatment such as transcutaneous electronic nerve stimulation. While this prior art allows ambulatory recording of pain at intervals over extended periods it has not allowed, nor suggested apparatus and methodology to acquire this pain information based on measured activity and to produce an indication of the relationship between pain intensity experienced by the patient and activity during daily living.

DETAILS OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention.

Figure 1:
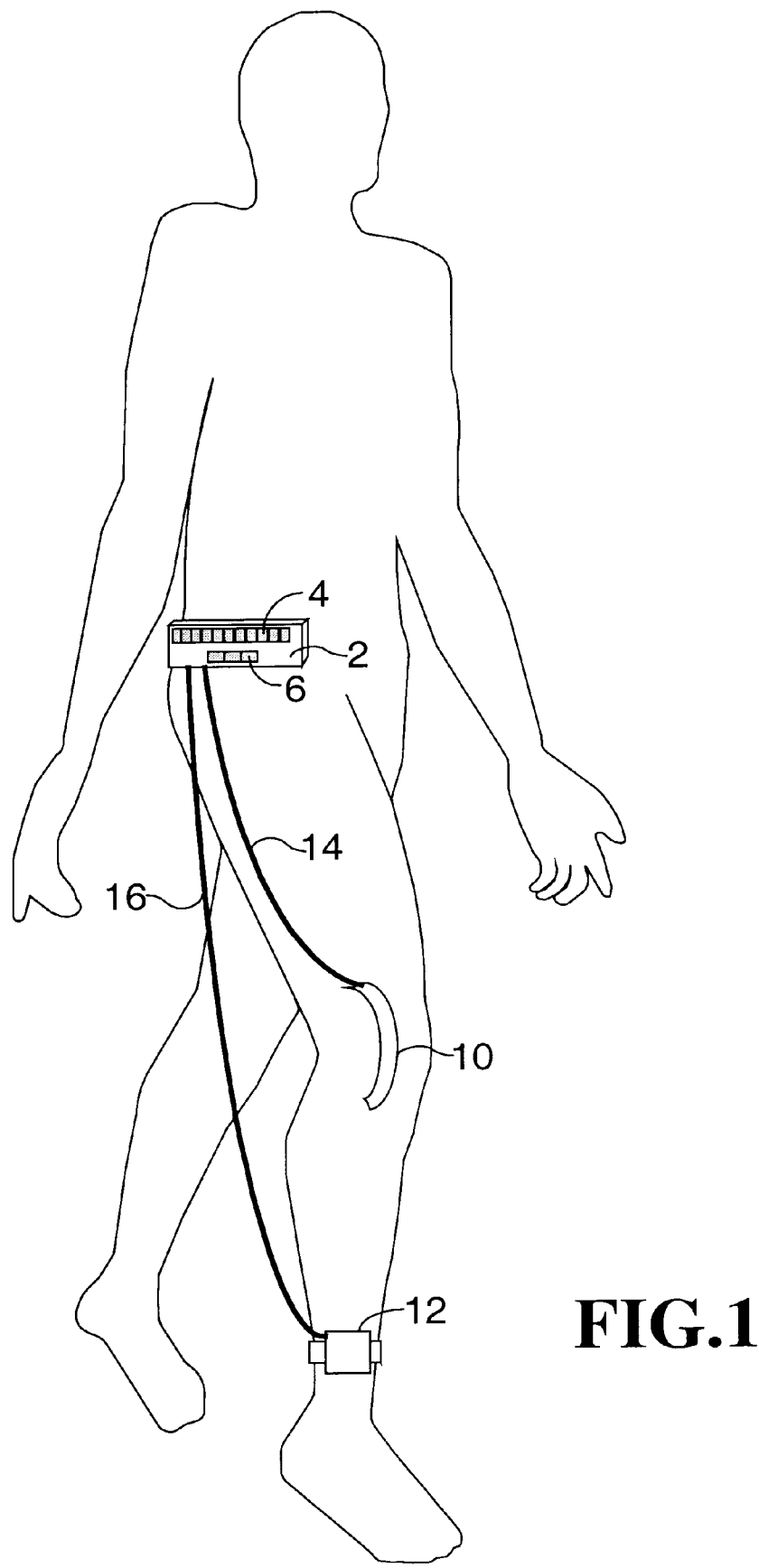
FIG. 1 shows the preferred embodiment of the invention applied to a patient to measure the relationship between knee pain and patient activity for assessing the outcome of knee surgery.

FIG. 1 depicts the invention applied to characterize activity involving the knee joint of a patient and to relate this characterized activity to pain associated with the knee joint. The invention includes a computing unit 2, which may be worn or carried by a patient. Integral to computing unit 2 is a pain level input 4 and an event input 6.

Pain level input 4 allows the patient to indicate the level of pain associated with the joint for which the pain and activity is to be related. In the preferred embodiment pain input 4 is a zero-to-ten scale of pain intensity and is comprised of eleven 1 cm by 1 cm membrane switches arranged in a row labeled 0 to 10. The patient is instructed to rate the pain they are experiencing on a 0 to 10 scale and press the correspondingly labeled membrane switch. Alternatively the preferred embodiment can be adapted to use other clinically accepted pain scales or combinations of scales as a pain level input. Examples of other scales include the ten-centimeter visual analog scale (VAS), verbal description scales and a 100 point digital scale. The patient is also instructed to enter a pain level indicative of the current pain they are experiencing in the affected knee joint in response to the activation of vibrating motor 8 as described further below, or at any other time at the discretion of the patient.

Event input 6 allows the patient to indicate that a predetermined event has occurred. Examples of predetermined events are the taking of certain medications by the patient and undergoing therapies such as applying heat to the joint.

Event input 6 is comprised of three membrane switches labeled "A", "B" and "C". The patient is instructed as to which events are to be associated with each membrane switch and is instructed to press the appropriate membrane switch when an event has occurred. Alternatively the preferred embodiment can be adapted to use other methodologies for event input 6, such as audio or video data acquisition to identify and record events. Similarly, event input 6 could comprise a number of discrete inputs sufficient to uniquely identify a plurality of events and can be labeled in any manner so as to allow identification of these events.

Figure 2:
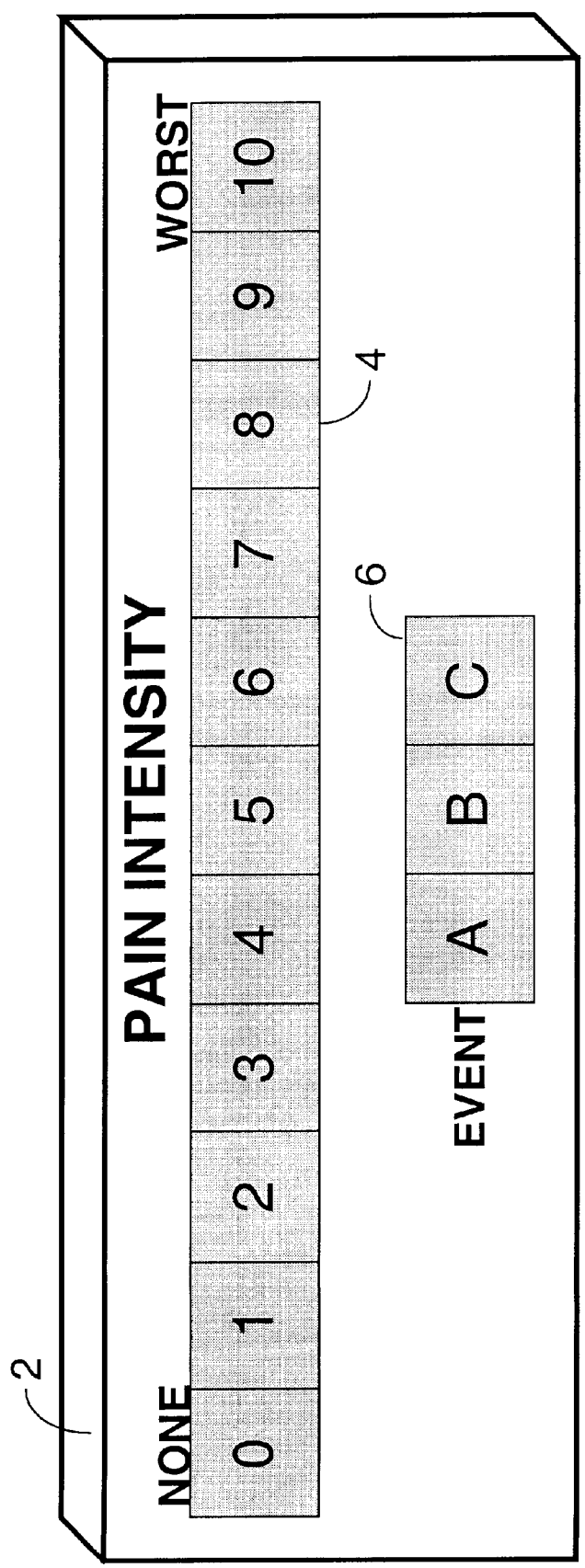
FIG. 2 is a detail of the face of the computing unit showing the membrane switches that comprise the pain level input and event input.

Refer to FIG. 2 for a depiction of the front face of computing unit 2 and details the layout of the membrane switches that comprise pain level input 4 and event input 6.

To characterize activity of the patient which involves use of the knee joint, computing unit 2 uses a combination of flexion sensor 10 and motion sensor 12. Flexion sensor 10 is shown in FIG. 1 applied to the knee of the patient. The sensor is affixed to the knee of the patient by disposable adhesive strips such that the sensor bends in proportion to the flexion angle of the knee, similar to applications described by Jackson in U.S. Pat. No. 4,444,205 and Gentile et al. in U.S. Pat. No. 5,086,785. In the preferred embodiment flexion sensor 10 is a bend-sensitive flexible resistor having a resistance that varies in proportion to its radius of curvature such that the resistance is 20K ohms at 0 degrees of knee flexion and 80K ohms at 90 degrees of knee flexion. Flexion sensor 10 comprises a flexible substrate for attachment to the limb and has a conductive elastomer laminated to the flexible substrate which exhibits a resistance which is proportional to its physical dimensions. Specifically, when the cross sectional area is altered, such as when the knee is flexed, a change in conductivity will take place in the elastomer material such that the greater the cross sectional area of the elastomer material, the greater the conductivity per unit length. Flexion sensor 10 produces a flexion signal the level of which is proportional to the angle of flexion of the knee. A multi-conductor electrical cable 14 connects flexion sensor 10 to computing unit 2. An electrical voltage is applied to the material through multi-conductor electrical cable 14 and the current, which is proportional to the change in resistance, is measured to determine the amount of bending of the flexion sensor 10 and produce a flexion signal the level of which is proportional to the angle of flexion of the knee. The flexion sensors utilized in the preferred embodiment are manufactured and distributed by Abrams Gentile Entertainment, New York, N.Y.

Alternatively it will be appreciated that a variety of apparatus can be utilized in order to produce a signal indicative of the flexion angle of the knee. Examples of alternate measurement apparatus include a goniometer equipped with a potentiometer producing a signal indicative of the angle between the two members of the goniometer; or inclinometers applied to the thigh and shin of the patient to measure the relative inclines of the femur and tibia thereby allowing flexion to be calculated.

Motion sensor 12 shown in FIG. 1 is applied to the ankle of the patient below flexion sensor 10. Motion sensor 12 comprises three individual accelerometers (ADXL05, Analog Devices, Norwood Mass.) which are oriented orthogonally. The accelerometers produce an output voltage signal which is proportional to their acceleration in the axis of sensitivity. These accelerometers are responsive to acceleration due to gravity, and therefore the output voltage signal which they produce also varies with the orientation of the sensors relative to the earth's gravitational field. In combination, the accelerometers produce signals having levels which are proportional to the acceleration of the motion sensor 12 relative to its surrounding environment in each of the x, y and z directions as well as proportional to its orientation relative to gravity. The DC component of the signal is representative of the orientation of the limb relative to gravity, and the AC component is due to accelerations of the limb relative to its surroundings as a result of patient activity. The sensor is applied on the patient such that the x direction corresponds to "forward" and the z direction corresponds to "upward" for a patient standing normally. A multi-conductor electrical cable 16 connects motion sensor 12 to computing unit 2. In the preferred embodiment motion sensor 12 is affixed to the ankle of the patient using an elastic strap. The levels of the acceleration signals produced by the three accelerometers are indicative of the magnitude of the vector components of acceleration of the ankle of the patient in each of the x, y, and z directions relative to the motion sensor 12, corresponding to forward, sideways and upward respectively, relative to the patient.

The preferred embodiment uses a combination of one flexion sensor and three accelerometers to characterize patient activity associated with use of the knee joint. This combination of sensors allows differentiation between different types of activity with precision and accuracy not possible using a single sensor. The signal from the accelerometer oriented to measure acceleration in the x direction and the signal from the accelerometer oriented to measure acceleration in the z direction are combined to differentiate the activities of reclining from other types of activities. The invention achieves this differentiation by first detecting acceleration cycles in the x direction indicative of steps in the forward direction to identify periods associated with ambulation and thereby not associated with reclining. For periods when no steps are detected, the invention uses the DC components of the measured accelerations, representative of tilt relative to a gravity reference, in both the x and z directions to compute the orientation of the limb and identify limb positions which are indicative of reclining. The combination of these sensors thereby allows the invention to differentiate periods of walking and reclining. The invention also uses the signals from the flexion sensor and the accelerometer oriented to measure acceleration in the x direction to differentiate between when the patient is walking on level ground and when they are climbing or descending stairs by first detecting steps then comparing the maximum flexion values associated with each step to a predetermined threshold. The preferred embodiment is utilized with alternate sensors in order to differentiate between and thereby characterize other types of patient activity. In addition, while the preferred embodiment provides details of sensors applied to characterize physical activity associated with use of the knee joint, the invention can be applied to other joints or to the human body as a whole. Such applications include but are not limited to the ankle, hip, wrist, shoulder and spine. For example, the invention can use the combination of a bend sensor and motion sensors to permit characterization of patient activity involving use of the spine and to produce an indication of the relationship between this activity and spinal pain experienced by the patient.

Figure 3:
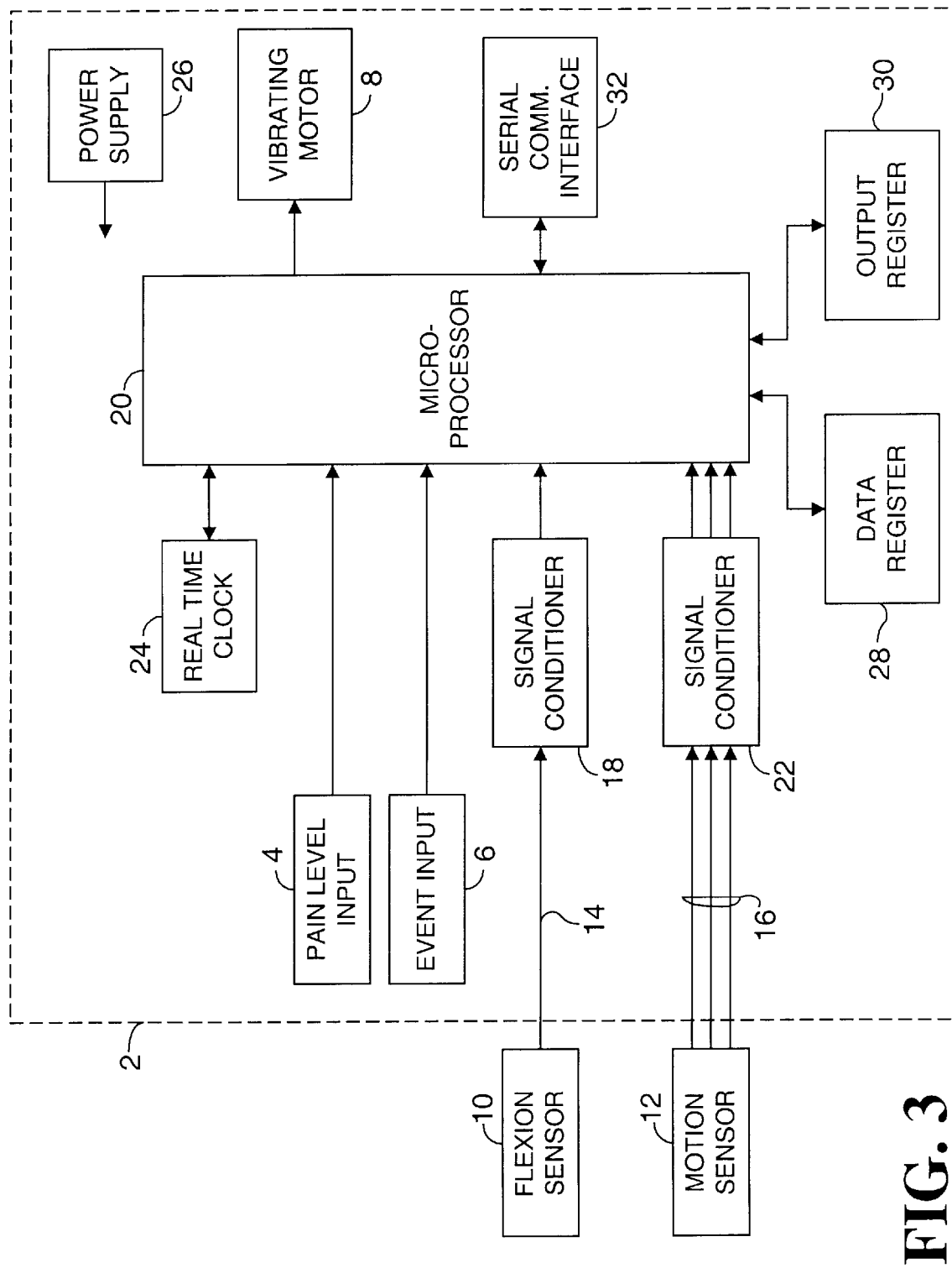
FIG. 3 is a block diagram of the preferred embodiment of the invention.

Referring to the block diagram of the preferred embodiment shown in FIG. 3, the flexion signal that is produced by flexion sensor 10 is communicated to signal conditioner 18 via multi-conductor electrical cable 14. Signal conditioner 18 amplifies the flexion signal so that it is suitable for communication to an analog to digital converter input of microprocessor 20 and also filters the flexion signal to remove unwanted noise. The amplified and filtered flexion signal from signal conditioner 18 is communicated to an analog to digital converter input of microprocessor 20. Acceleration signals from the accelerometers which comprise motion sensor 12 are communicated to signal conditioner 22 via multi-conductor electrical cable 16. Signal conditioner 22 amplifies and filters the levels of the acceleration signals so that they are suitable for communication to an analog to digital converter inputs of microprocessor 20. It will be appreciated that a variety of alternate means exist for communicating acceleration signals from motion sensor 12 to signal conditioner 22 and from flexion sensor 10 to signal conditioner 18 such as infrared and wireless telemetry. Any such means is acceptable and can be used in place of the described multi-conductor electrical cables 14 and 16.

Electrical signals from the eleven membrane switches that comprise pain level input 4 are communicated to a digital input port of microprocessor 20. Under the control of operating software, microprocessor 20 can determine when a switch representative of a pain level has been depressed. Electrical signals from the three membrane switches that comprise event input 6 are communicated to another digital input port of microprocessor 20. Under the control of operating software, microprocessor 20 can determine when switch representative of a predetermined event has been depressed.

Real time clock 24 shown in FIG. 3 maintains the current time and date, and includes a battery as an alternate power source such that clock operation continues during any interruption in the supply of electrical power from power supply 26 required for the normal operation of computing unit 2. Microprocessor 20 communicates with real time clock 24 for both reading and setting the current time and date.

Microprocessor 20 communicates with data register 28 to store and retrieve data obtained from pain level input 4, event input 6, flexion sensor 10, motion sensor 12 and real time clock 24 as described below. Microprocessor 20 also communicates with output register 30 to store and retrieve data indicative of the relationship between measured activity, pain and events for output as described below.

Computing unit 2 includes a serial communications interface 32 to communicate data to an external computer or other apparatus for display, archival storage and further analysis. Microprocessor 20 communicates with serial communications interface 32 to transmit and receive data as determined by the operating software of microprocessor 20.

Vibrating motor 8 is electrically connected through suitable driver electronics to a digital output port of microprocessor 20. Vibrating motor 8 is of similar design to the vibrating motors commonly used as silent signaling devices in personal pagers. Microprocessor 20 under the control of operating software as described below can activate vibrating motor 8 to signal the patient when a pain level is to be entered. Other signaling means such as an audible tone generator or flashing light may be used in addition to, or in place of, vibrating motor 8 to signal the patient to enter a pain level.

Power supply 26 provides regulated DC power for the normal operation of all electronic and electrical components associated with the invention.

Figure 4:
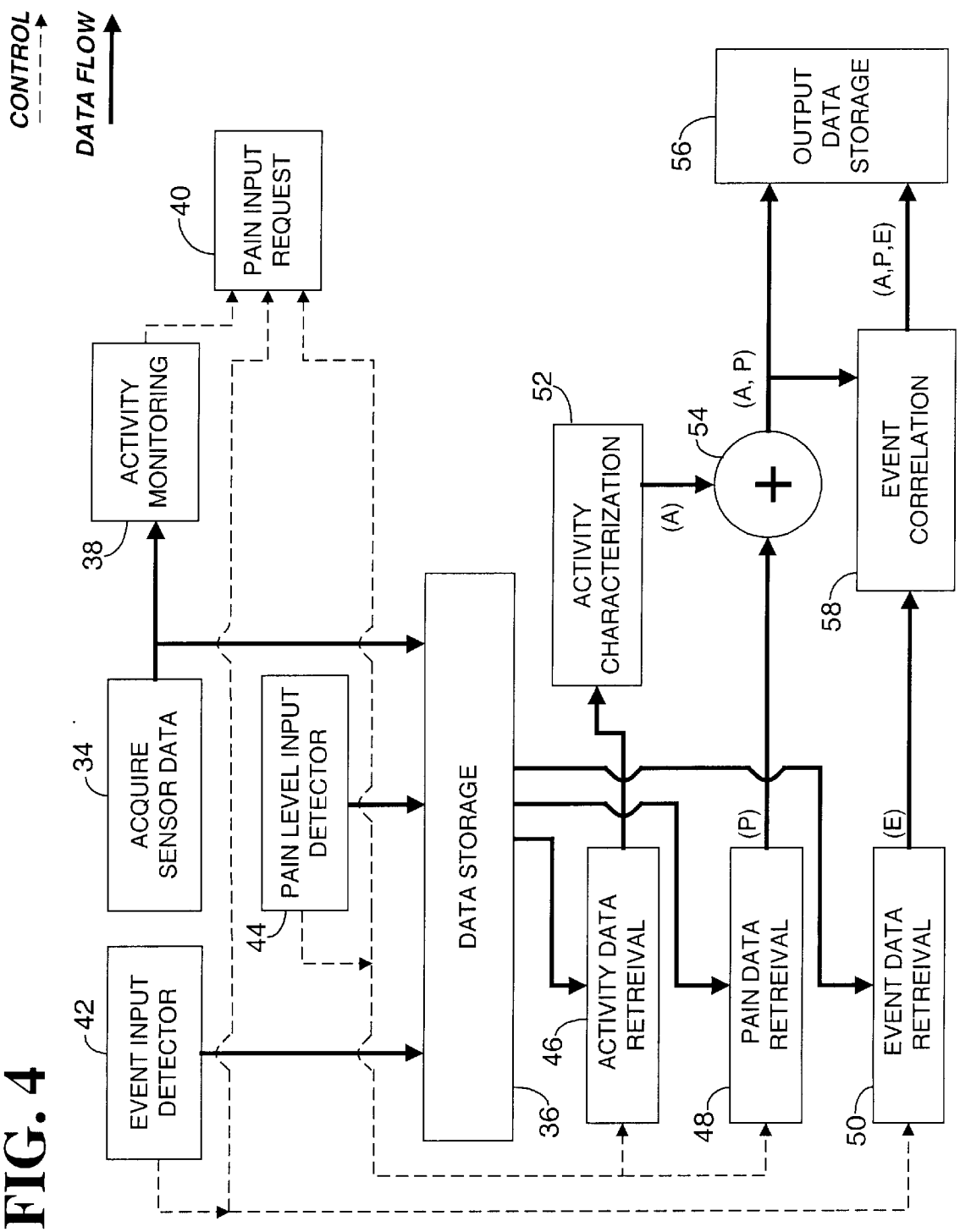
FIG. 4 is a functional diagram showing operation of the preferred embodiment's software modules.

FIG. 4 is a software flow diagram illustrating the data flow and communication between the software modules which comprise the operating software of the preferred embodiment and which are carried out by microprocessor 20 during normal operation. In FIG. 4, solid lines are used to represent the flow of data between individual software modules and dashed lines are used to represent communication pathways between the individual software modules to control the flow of data.

When first activated, microprocessor 20 operates in an initialization mode for a predetermined time period of 5 minutes. During this period microprocessor 20 suspends all other operations described below and initializes data storage registers used in the characterization of activity levels as described below. After this initialization period, the invention operates as described in the following paragraphs.

Referring to FIG. 4, microprocessor 20 operates to sample the level of the flexion signal from flexion sensor 10 and the levels of the acceleration signals from motion sensor 12 by executing the acquire sensor data software module 34. The acquire sensor data software module 34 produces samples of the level of these signals at a rate of 20 Hz. Each time acquire sensor data software module 34 produces samples of the flexion and acceleration signal levels, microprocessor 20 reads from real time clock 24 the current time. Digital representations of the sampled level of the flexion signal, level of the acceleration signals and clock time are then communicated to data storage software module 36 for storage in data register 28

As shown in FIG. 4, data acquired from the activity sensors is also communicated by microprocessor 20 to activity monitoring software module 38. Activity monitoring software module 38 maintains in a data register the most recent 6,000 samples of the level of the flexion signal and the most recent 6,000 samples of the levels of the acceleration signals in each of the x, y and z directions as defined above. Each time samples of the level of the flexion and acceleration signals are added to the register, activity monitoring software module 38 computes the number of flexion cycles (where a flexion cycle is a flexing and un-flexing of the joint) which have occurred in the preceding 5 minute interval by calculating the number of positive-to-negative slope transitions that occur in the samples of the level of the flexion signal maintained in the data register. A positive-to-negative slope transition is defined as a change in the slope (change in signal magnitude per unit time) of the flexion signal from a positive to a negative value, which indicates a point at which the flexion angle changes from increasing in magnitude to decreasing in magnitude. This is indicative of the point at which the patient begins to straighten the leg at the end of each step.

In the preferred embodiment the slope is determined over 10-sample segments in order to reduce the effect of signal noise and sample jitter and alternate numbers of samples can be used for calculating the slope segments in order to change the sensitivity of the invention to small movements of the knee joint. Each time samples of the level of the flexion and acceleration signals are added to the register, activity monitoring module 38 also computes the average level of all of the acceleration signals during the preceding 5 minute interval. This average of the acceleration signals is indicative of the average level of motion over the 5 minute time period.

Activity monitoring software module 38 uses the computed number of flexion cycles and the computed average level of motion to determine when to initiate the execution of pain input request software module 40 by microprocessor 20 described below.

Activity monitoring software module 38 maintains maximum and minimum motion registers. Each time activity monitoring software module 38 computes the average level of motion using the most recent 6000 samples of the acceleration signals it is compared to levels stored in the maximum motion and minimum motion registers. If the average level of motion exceeds the level stored in the maximum motion register the average level of motion is stored in the maximum motion register. Similarly, if the average level of the motion falls below the level stored in the minimum motion register the average level of motion is stored in minimum motion register.

Each time activity monitoring software module 38 computes the average level of motion activity monitoring software module 38 also subtracts the level stored in the minimum motion register from the level stored in the maximum motion register and compares the difference to a predetermined motion threshold. If the difference exceeds this predetermined motion threshold, microprocessor 20 initiates the execution of pain input request software module 40 and then stores the average level of the motion in both the maximum motion register and the minimum motion register.

Activity monitoring software module 38 operates similarly to maintain maximum and minimum flexion cycle registers, compare the difference in the levels stored in these registers to a predetermined flexion threshold and initiate the execution of pain input request software module 40 when the difference exceeds the predetermined flexion threshold.

By operating in this manner the preferred embodiment is responsive to the activity of the patient to acquire a pain level input when a significant change in the components of activity of the patient described is observed. Microprocessor 20 initiates the execution of pain input request software module 40 in response to activity monitoring software module 38 as described above and in response to event input detector software module 42 described below.

Pain input request software module 40 activates vibrating motor 8 for 5 seconds to indicate to the patient that a pain level is to be entered via pain input 4. Pain input request software module 40 continues to activate vibrating motor 8 every 60 seconds until microprocessor 20 suspends execution of pain input request software module 40 in response to pain level input detection software module 44 detecting that a pain level has been entered as described below or when a predetermined time-out interval of 5 minutes has elapsed.

Pain level input detector software module 44 detects when the patient has depressed one of the membrane switches comprising pain level input 4 to enter a pain level. When a pain level is entered by the patient, pain level input detector software module 44 operates as follows: (a) reads the current time from real time clock 24 and communicates a digital representation of the entered pain level and the corresponding time value to data storage software module 36 for storage in data register 28; (b) acts to suspend the execution of pain input request software module 40 if pain input request software module 40 is executing; (c) initiates the execution of activity data retrieval software module 46 described below; and (d) initiates the execution of pain data retrieval software module 48 described below.

Similarly, event input detector software module 42 detects when the patient has depressed one of the membrane switches comprising event input 6 to enter an event. When an event is entered by the patient, event input detector software module 42 operates as follows: (a) reads the current time from real time clock 24 and communicates a value identifying the entered event and the corresponding time value to data storage software module 36 for storage in data register 28; (b) acts to initiate the execution of pain input request software module 40; and (c) initiates the execution of event data retrieval software module 50 described below.

Microprocessor 20 executes activity data retrieval software module 46 in response to pain level input detector software module 44. Activity data retrieval software module 46 communicates with data storage software module 36 to retrieve from data register 28 the last 6,000 levels of the flexion and acceleration signals representing the activity of the knee joint during the 5 minute interval preceding the time at which the pain level input detector module 44 detected that a pain level was entered. Activity data retrieval software module 46 communicates the retrieved data to activity characterization software module 52.

Activity characterization software module 52 analyzes the combination of retrieved samples of the signals from flexion sensor 10 and the accelerometers which comprise motion sensor 12 to characterize the activity level of the patient during the preceding 5 minute interval. In the preferred embodiment, patient activity is characterized in terms of the following scale:

| LEVEL | DESCRIPTION |
|---|---|
| 1. | Minimal walking and frequently reclining. |
| 2. | Minimal walking and occasionally reclining. |
| 3. | Limited walking and frequently reclining. |
| 4. | Limited walking and occasionally reclining. |
| 5. | Moderate walking and frequently reclining. |
| 6. | Moderate walking and occasionally walking. |
| 7. | Frequent walking and normal average step rate. |
| 8. | Frequent walking and high average step rate. |
| 9. | Very frequent walking and normal average step rate. |
| 10. | Very frequent walking and high average step rate. |

This scale is representative of those which appear on outcomes questionnaires and of questions typically asked by a clinician during the routine interview and examination of a patient. For the purpose of this characterization, "reclining" is defined as sitting or lying down in such a way so that the lower legs are in a position which is within 45 degrees of horizontal. "Minimal walking" is defined to be less than 10 steps over a 5 minute period, "Limited walking" is defined as 10–20 steps over a 5 minute period, "Moderate walking" as 20–50 steps over a 5 minute period, "Frequent walking" as 50–100 steps over a 5 minute period and "Very frequent walking" as greater than 100 steps over a 5 minute period. "Normal average step rate" is defined to be less than 30 steps/minute and "high average step rate" is defined to be greater than 30 steps/minute. Similarly "frequently reclining" is defined as reclining for greater than 50% of the time over the 5 minute period, and "occasionally reclining" as less than 50% of the time.

Activity characterization software module 52 uses the combination of 6000 samples of the flexion and acceleration signals in the x, y and z directions retrieved from data register 28 to differentiate between different types of patient activity in order to characterize the activity of the patient in terms of the activities described above. By using the combination of the retrieved samples of flexion signals and acceleration signals in the x, y and z directions for analysis, activity characterization software module 52 is able to differentiate between activities with validity and accuracy not possible if only one sensor was used. The invention achieves this differentiation by first detecting acceleration cycles in the x direction indicative of steps in the forward direction to identify and characterize periods associated with walking. When the patient takes a step, the acceleration of the lower leg suddenly increases in the forward direction as the patient begins to move the leg forward, then suddenly decreases as the forward motion of the leg slows in order for the foot to make contact with the ground at the end of the step. This activity of taking a step produces a rise and fall in acceleration in the x direction as measured by motion sensor 12. Activity characterization software module 52 operates to detect steps by comparing the magnitude of the AC component of the x direction acceleration signal to a predetermined threshold and incrementing a counter each time the threshold is exceeded. A predetermined latency period of 0.5 seconds, during which the counter is disabled after each step is detected prevents multiple counting of a single step after the threshold is first exceeded. By identifying steps over the 5 minute, 6000 sample period, activity characterization software module 52 is able to identify periods within this sample of walking and characterize these periods in terms of step rate. For periods during the sample when no steps are detected as described above, the invention uses the DC components of the measured accelerations in both the x and z directions, indicative of the orientation of motion sensor 12 relative to a gravity reference, to compute the orientation of the limb in order to identify limb positions which are indicative of the patient reclining. During periods when there are no steps and when the orientation of motions sensor 12 as indicated by the DC components of the measured acceleration signals in the x and z directions is found to be greater than 45 degrees from vertical, the patient is determined to be reclining. The combination of these sensors thereby allows the invention to differentiate periods of walking and reclining and thereby characterize the activity of the patient over the 5 minute period in terms of the quantitative scale provided above. If only the signal from a single accelerometer was available, these activities could not be reliably differentiated.

While a predetermined time of 5 minutes has been chosen as the interval over which activity levels are computed for comparison and relation to pain, other times may be used.

Microprocessor 20 executes pain data retrieval software module 48 in response to pain level input detector software module 44. Pain data retrieval software module 48 communicates with data storage software module 36 to retrieve from data register 28 the most recent pain level entered by the patient.

As shown in FIG. 4 the pain level retrieved by pain data retrieval software module 48 is combined 54 with characterized activity level computed by activity characterization software module 52 to produce a two element data set of the form (A, P) where A corresponds to the level of activity over the 5 minute period immediately preceding entry of a pain level by the patient and P corresponds to the pain level.

The levels of the combined data set are communicated to output data storage software module 56 for storage in output register 30 and also communicated to event correlation software module 58.

Microprocessor 20 executes event data retrieval software module 50 in response to event input detector software module 42 detecting the entry of an event by the patient. Event data retrieval software module 50 communicates with data storage software module 36 to retrieve the value identifying the last event entered by the patient for communication to event correlation software module 58.

Event correlation software module 58 maintains an event register. When event correlation software module 58 receives a value identifying an event from event data retrieval software module 50, event correlation software module 58 stores the received value in the event register for a predetermined time period of 5 minutes. If the event register contains values identifying an events when event correlation software module 58 receives a two element data set of the form (A, P) described above and as shown in FIG. 4, event correlation software module 58 produces three element data sets of the form (A, P, E) for each value in the event register where A and P are defined as above and E is the value identifying an event entered by the patent in the preceding 5 minutes. As shown in FIG. 4 the three element data sets are communicated to output data storage software module 56 for storage in output data register 30.

The preferred embodiment of the invention is intended to be worn and used by a patient for predetermined time period of seven days in order to produce a series of data sets of the form (A, P) and (A, P, E) which are stored in output register 30. Alternatively, the invention may be adapted to be worn and used by a patient for longer or shorter time periods or for specified time intervals during a predetermined time period. The data sets stored in output register 30 are indicative of the relationship between pain, characterized activity and specified events over the data collection period. Data stored in output register 30 may be retrieved by microprocessor 20 and communicated to an external computer for analysis and display via serial communication interface 32.

Figure 5B:
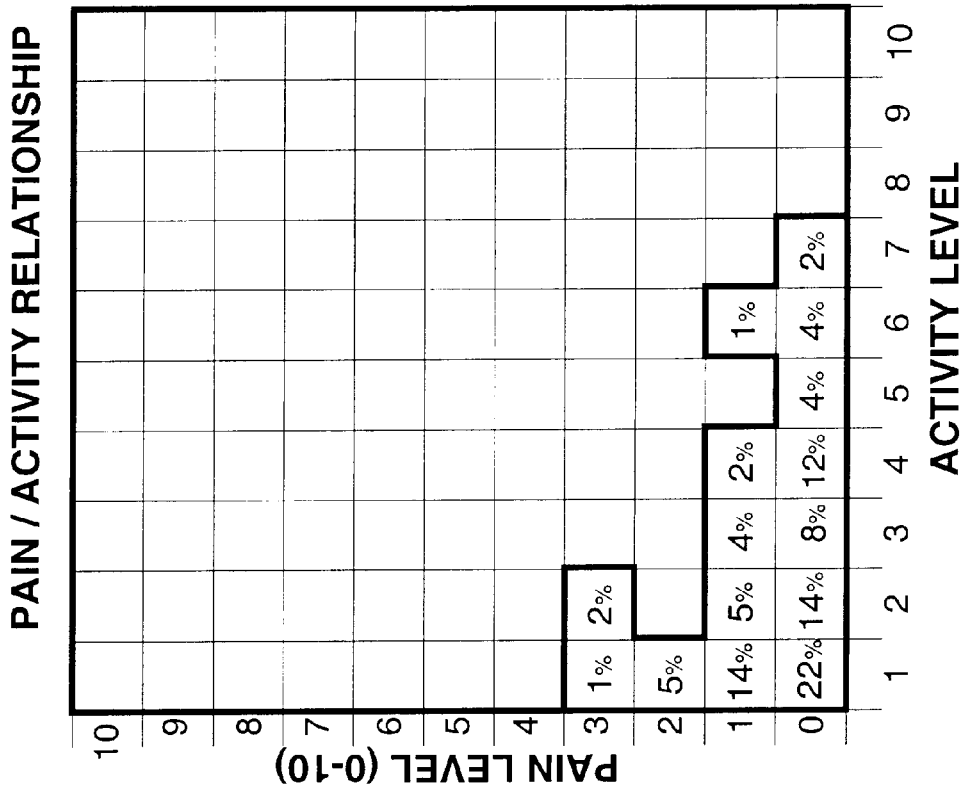
FIG. 5a and FIG. 5b are example graphical representations of the relationship between pain and activity for a patient with osteoarthritis of the knee.
Figure 5A:
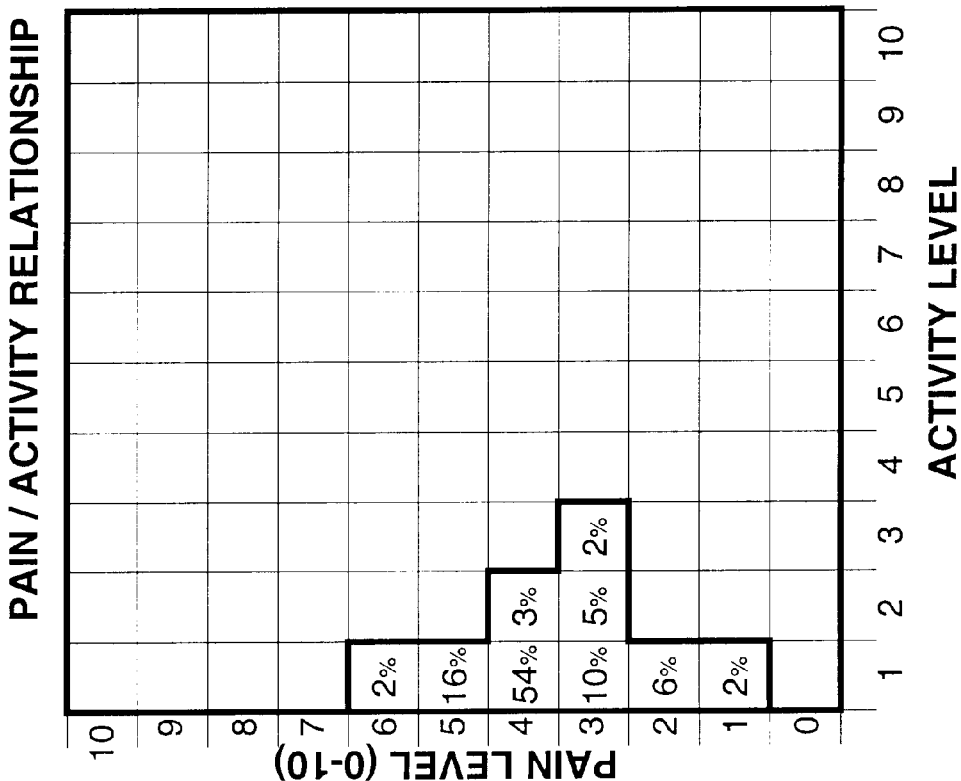

The relationship between pain and activity for a given patient is shown can be shown graphically as a matrix. An example graphical matrix is shown in FIG. 5a. In the matrix depicted in FIG. 5a, each entry indicates the percentage of the total number of (A, P) sets which fall within the boundaries of that element. Where there is no entry, no sets fall within that element. The sum of all entries is 100%. To illustrate, the entry "54%" in the (activity=1, pain=4) element indicates that 54% of all (A,P) sets acquired during the measurement period indicated a pain intensity level of "4" while the knee was at an activity level of 1. The graphical matrix shown in FIG. 5a is representative of a typical patient before undergoing knee joint replacement surgery for treatment of osteoarthritis. The graphical matrix shown in FIG. 5b is representative of the relationship between pain and activity for the same patient one year after surgery and shows a marked reduction in the level of pain associated with all levels of activity.

Figure 6B:
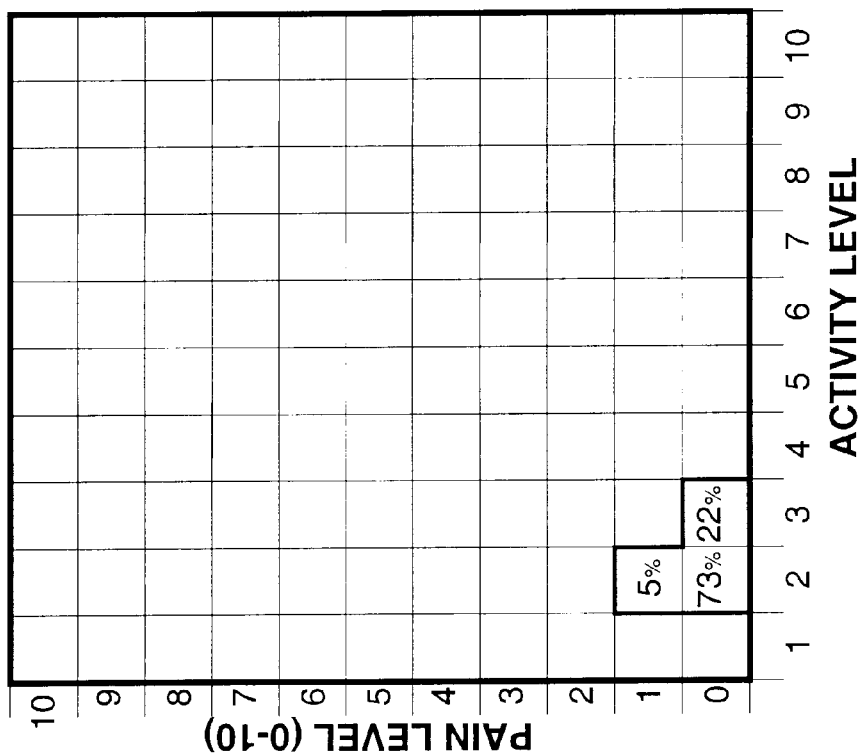
FIG. 6a and FIG. 6b are example graphical representations of pain, activity, event relationship.
Figure 6A:
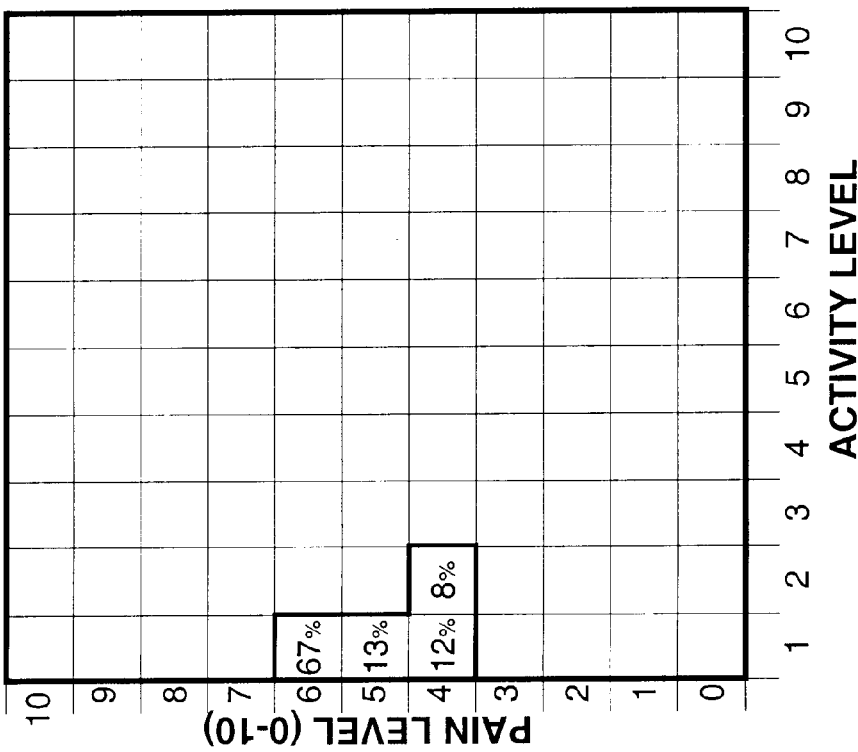

As shown in FIGS. 6a and 6b (A,P,E) sets can be graphically represented similarly with each matrix displaying information related to the occurrence of a specific event. In FIGS. 6a and 6b graphical matrixes showing the pain activity relationship are presented for all occurrences of event "A" which has been defined as taking a specific pain medication. The graphical matrix shown in FIG. 6a is representative of the same patient as in FIGS. 5a and 5b before undergoing knee joint replacement surgery. The graphical matrix shown in FIG. 6b is representative of the same patient one year after surgery and shows a marked change in the pain/activity relationship associated with this event as a result of treatment.

Alternatively the graphical matrixes shown in FIGS. 5a, 5b, 6a and 6b can be shown as density graphs in which each element is shaded or patterned in proportion to the corresponding percentage of sample sets which fall within that element.

While the preferred embodiment has described the use of the signals from a combination of a flexion sensor and three accelerometers to characterize patient activity in terms of the previously described scale, alternate sensors are utilized in order to differentiate between other types of patient activity. In addition, while the preferred embodiment provides details of sensors applied to characterize physical activity associated with use of the knee joint, the invention may be applied to other joints or to the human body as a whole. Such applications include but are not limited to the ankle, hip, wrist, shoulder and spine.

Figure 7:
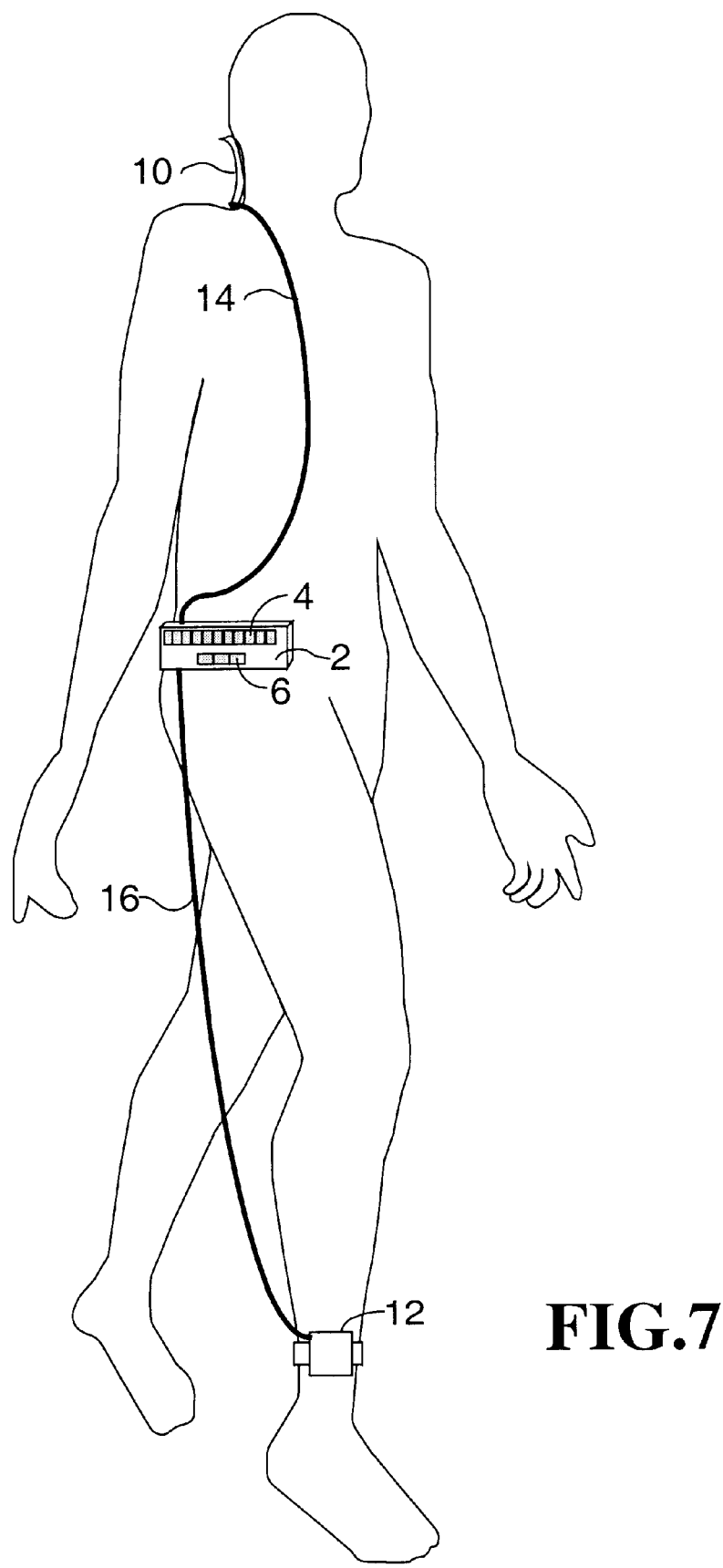
FIG. 7 shows the preferred embodiment of the invention applied to a patient in order to measure the relationship between neck pain and activity for assessing the outcome of a treatment for neck injury.

For example, FIG. 7. shows the invention applied to relate neck pain and activity in a patient in order to evaluate the outcome of a treatment for neck (cervical spine) injury. In this application flexion sensor 10 is applied to the neck of the patient in order to produce a signal indicative of the flexion of the cervical spine. Activity monitoring software module 38 operates in a manner identical to that described previously in order to initiate the execution of pain input request software module 40. Activity characterization software module 52 operates in a manner similar to that described above in order to characterize activity of the patient in terms of a scale consistent with routine clinical practice for evaluating neck injury using the combination of signals from flexion sensor 10 applied at the neck and motion sensor 12 applied at the ankle. In this manner the invention characterizes and differentiates between different types of activity involving use of the cervical spine and produces an indication of the relationship between this activity and pain experienced by the patient.

We claim:

1. Apparatus for relating pain and activity experienced by a patient, comprising:

pain transducing means for allowing a patient to select any one pain level from a predetermined number of pain levels and for producing a pain level signal indicative of the selected level;

activity transducing means for measuring a level of a parameter of a physical activity of the patient and for producing an activity parameter level signal indicative of the measured level of the parameter;

patient request means for comparing the activity parameter level signal with a predetermined threshold level and signaling the patient to select a pain level when the activity parameter level signal exceeds the threshold level; and relating means responsive to the pain level signal and the activity parameter level signal for characterizing the activity of the patient corresponding to the selected level of pain to be one activity level of a predetermined number of predefined activity levels and for producing a signal indicative of the characterized level of activity and the corresponding pain level.

2. The apparatus of claim 1 wherein the activity transducing means further measures a level of a second parameter of the activity at the time corresponding to the selection of the pain level and further produces a second activity parameter level signal indicative of a measured level of the second parameter of the activity, and wherein the relating means is further responsive to the second activity parameter level signal.

3. The apparatus of claim 1 wherein the activity transducing means comprises a motion sensor affixed to a part of the body of the patient near a predetermined location.

4. The apparatus of claim 1 wherein the activity transducing means comprises a flexion sensor and a motion sensor applied to the patient.

5. The apparatus of claim 1 wherein the activity transducing means comprises a plurality of sensors for measuring a combination of physiological parameters.

6. The apparatus of claim 1 wherein the apparatus further includes a patient interface operable by the patient to indicate the occurrence of a predefined event and where the relating means further relates the occurrence of the predefined event to the associated level of activity and pain.

7. The apparatus of claim 1 wherein the device further includes a means to compare the measured relationship between pain and activity at one time to the measured relationship between pain and activity at a second time.

8. Apparatus for relating pain and activity experienced by a patient, comprising:

activity transducing means for measuring a level of a parameter of a physical activity of a patient and for producing an activity parameter level signal indicative of the measured level of the parameter;

pain transducing means responsive to the activity parameter level signal for producing a patient signal perceptible by the patient and including input means for allowing the patient to select any one pain level from a predetermined number of pain levels to correspond to the measured level of the parameter, and for producing a pain level signal indicative of the selected pain level; and relating means responsive to the pain level signal and the activity parameter level signal for characterizing the activity of the patient corresponding to the selected level of pain to be one activity level of a predetermined number of predefined activity levels and for producing a signal indicative of the characterized level of activity and the corresponding pain level.

9. The apparatus of claim 8 wherein the activity transducing means further measures a level of a second parameter of the activity at the time corresponding to the selection of the pain level and further produces a second activity parameter level signal indicative of a measured level of the second parameter of the activity, and wherein the relating means is further responsive to the second activity parameter level signal.

10. The apparatus of claim 8 wherein the activity transducing means comprises a motion sensor affixed to a part of the body of the patient near a predetermined location.

11. The apparatus of claim 8 wherein the activity transducing means comprises a flexion sensor and a motion sensor applied to a patient.

12. The apparatus of claim 8 wherein the activity transducing means comprises a plurality of sensors for measuring a combination of physiological parameters.

13. The apparatus of claim 8 wherein the apparatus further includes a patient interface operable by the patient to indicate the occurrence of a predefined event and where the relating means further relates the occurrence of the predefined event to the associated level of activity and pain.

14. Apparatus for relating pain and activity experienced by a patient, comprising:

a patient interface operable by the patient to indicate the occurrence of a predefined event wherein the predefined event is the performance of a specified physical activity;

activity transducing means for measuring a level of a parameter of a physical activity of a patient and for producing an activity parameter level signal indicative of the measured level of the parameter;

pain transducing means responsive to the activity parameter level signal for producing a patient signal perceptible by the patient and including input means for allowing the patient to select any one pain level from a predetermined number of pain levels to correspond to the measured level of the parameter, and for producing a pain level signal indicative of the selected pain level; and relating means responsive to the pain level signal and the activity parameter level signal for and relating the occurrence of the predefined event to the associated level of activity and pain and for characterizing the activity of the patient corresponding to the selected level of pain to be one activity level of a predetermined number of predefined activity levels and for producing a signal indicative of the characterized level of activity and the corresponding pain level.

15. The apparatus of claim 8 wherein the device further includes a means to compare the measured relationship between pain and activity at one time to the measured relationship between pain and activity at a second time.

16. A method of relating pain and activity experienced by a patient, comprising the steps of:

measuring a level of a parameter of a physical activity of a patient;

producing a patient signal perceptible by the patient in response to the measured level of the parameter of the physical activity exceeding a threshold level;

allowing the patient to select any one pain level from a predetermined number of pain levels when the patient signal is perceived by the patient;

characterizing the activity of the patient corresponding to the selected level of pain to be one activity level of a predetermined number of predefined activity levels; and producing a signal indicative of the characterized level of activity and the corresponding pain level.

* * * * *